(12) United States Patent
Kim

(10) Patent No.: US 12,211,591 B2
(45) Date of Patent: Jan. 28, 2025

(54) FIRST-PRINCIPLES-DERIVED EFFECTIVE MASS APPROXIMATION SIMULATION METHOD AND SYSTEM FOR ACCURATE AND EFFICIENT COMPUTATIONAL DESIGN OF ELECTRONIC STRUCTURE AND OPTICAL PROPERTIES OF QUANTUM NANOSTRUCTURES

(71) Applicant: Korea Advanced Institute of Science and Technology, Daejeon (KR)

(72) Inventor: Yong-Hoon Kim, Daejeon (KR)

(73) Assignee: Korea Advanced Institute of Science and Technology, Daejeon (KR)

(*) Notice: Subject to any disclaimer, the term of this patent is extended or adjusted under 35 U.S.C. 154(b) by 383 days.

(21) Appl. No.: 17/522,424

(22) Filed: Nov. 9, 2021

(65) Prior Publication Data
US 2022/0180977 A1   Jun. 9, 2022

(30) Foreign Application Priority Data

Nov. 10, 2020 (KR) .......................... 10-2020-0148999
Oct. 15, 2021 (KR) .......................... 10-2021-0137711

(51) Int. Cl.
*G16C 10/00*   (2019.01)
(52) U.S. Cl.
CPC .................................. *G16C 10/00* (2019.02)
(58) Field of Classification Search
CPC ........ G16C 10/00; G16C 20/30; G16C 60/00; G06F 30/36; G06F 30/367; G06F 2111/14
See application file for complete search history.

(56) References Cited

U.S. PATENT DOCUMENTS

| | | | | |
|---|---|---|---|---|
| 11,023,639 | B2 * | 6/2021 | Stokbro | G06F 30/36 |
| 2011/0313741 | A1 * | 12/2011 | Langhoff | G16C 20/30 |
| | | | | 703/2 |
| 2018/0096085 | A1 * | 4/2018 | Rubin | G16C 10/00 |

OTHER PUBLICATIONS

Hyeonwoo Yeo et al., "First principles-derived effective mass approximation for the improved description of quantum nanostructures," J. Phys. Mater. 3 (2020) 034012 (https://doi.org/10.1088/2515-7639/ab9b61).

* cited by examiner

*Primary Examiner* — An H Do
(74) *Attorney, Agent, or Firm* — ArentFox Schiff LLP; Joseph M. Maraia; Marlo Schepper Grolnic

(57) ABSTRACT

The present concept relates to a first principle-derived effective mass approximation simulation technology for accurate and efficient computational simulation of an optical property of a quantum nanostructure including creating an effective mass approximation (EMA) parameter through first principle density functional theory (DFT) calculation for a model nanostructure corresponding to a simulation target quantum nanostructure, performing EMA calculation using the EMA parameter created through the DFT calculation, and acquiring the optical property of the quantum nanostructure based on an electronic structure generated through the EMA calculation.

18 Claims, 13 Drawing Sheets

(a)

(b)

(c)

FIRST-PRINCIPLES-DERIVED EFFECTIVE MASS APPROXIMATION SIMULATION METHOD AND SYSTEM FOR ACCURATE AND EFFICIENT COMPUTATIONAL DESIGN OF ELECTRONIC STRUCTURE AND OPTICAL PROPERTIES OF QUANTUM NANOSTRUCTURES

CROSS-REFERENCE TO RELATED APPLICATIONS

A claim for priority under 35 U.S.C. § 119 is made to Korean Patent Application No. 10-2021-0137711 filed on Oct. 15, 2021, in the Korean Intellectual Property Office, and Korea Patent Application No. 10-2020-0148999 filed on Nov. 11, 2020, in the Korean Intellectual Property Office, the entire contents of which are hereby incorporated by reference.

BACKGROUND

Embodiments of the inventive concept described herein relate to a first principle-derived effective mass approximation simulation method and a system thereof, and more particularly, relate to a first principle-derived effective mass approximation simulation technology for accurate and efficient computational simulation of an optical property of a quantum nanostructure.

With a development of nanofabrication and synthesis techniques, it is now possible to prepare semiconductor nanostructures with various sizes and shapes to adjust electronic and optical properties thereof. In such nanostructure experiencing quantum and dielectric limiting effects, functions useful for various device applications such as a light emitting diode (LED), a light sensor, a solar cell, solar fuel production, and biological labeling may be acquired by designing an exciton. In particular, it is possible to further modulate the optical property by inducing various external stimuli such as an electric field and a magnetic field, which makes the semiconductor nanostructure a promising candidate for display application.

Computer simulation has played an important role in characterization and design of the semiconductor nanostructure. In this connection, the computer simulation is, in principle, performed with a first principle system such as many-body or quantum Monte Carlo simulations performed on a density functional theory (DFT). However, in practice, the DFT and DFT-based high-level calculation that require very large calculational resources are often too cumbersome or impossible to be applied to a nanostructure of an actual size. Therefore, approximation methods such as an effective mass approximation (EMA) and a strict coupling technique are still routinely used for study and design of a large-scale complex semiconductor nanostructure. However, the EMA approach using an effective mass and a dielectric constant derived from bulk crystals often fails to produce an accurate and reliable result for the nanostructure experiencing the quantum and dielectric limiting effects.

The effective mass approximation (EMA) may become an efficient method for calculational study of a semiconductor nanostructure that is too large to be processed by first principle calculation, but a plan to accurately and stably introduce an EMA parameter for the given nanostructure remains to be devised.

Accordingly, the inventive concept proposes an EMA approach based on first principle-derived data that may accurately predict an optoelectronic property of a quantum nanostructure.

SUMMARY

Embodiments of the inventive concept is to extend an EMA simulator based on a grid-based object-oriented real-space engine (OORE) for electronic structure calculation using an EMA parameter created in first principle calculation of a nanostructure.

According to an exemplary embodiment, a first principle-derived effective mass approximation simulation method for accurate and efficient computational simulation of an optical property of a quantum nanostructure includes creating an effective mass approximation (EMA) parameter through first principle density functional theory (DFT) calculation for a model nanostructure corresponding to a simulation target quantum nanostructure, performing EMA calculation using the EMA parameter created through the DFT calculation, and acquiring the optical property of the quantum nanostructure based on an electronic structure generated through the EMA calculation.

The quantum nanostructure may include a zero-dimensional quantum dot, a one-dimensional nanorod, and a two-dimensional nanoplatelet.

The EMA parameter may include effective electron and hole masses, a dielectric constant or a position-dependent dielectric function, a smoothed EMA envelope potential.

The creating of the EMA parameter through the DFT calculation may include performing first principle DFT calculation of the model nanostructure corresponding to the quantum nanostructure to extract a dielectric constant or a position-dependent dielectric function, electron and hole masses, and an EMA envelope potential obtained by smoothing a DFT-Kohn-Sham potential of the quantum nanostructure.

In the model nanostructure corresponding to the quantum nanostructure, an effective mass and the dielectric constant/function may be extracted from a nanoplate and a nanorod, and from a two-dimensional nanosheet with the most corresponding size and composition in a case of a quantum dot, and the EMA envelope potential may be extracted from a nanosheet infinitely extending in a two-dimension in the case of the nanoplate, a nanowire infinitely extending in a one-dimension in the case of the nanorod, and a zero-dimensional quantum dot in the case of the quantum dot.

The creating of the EMA parameter through the DFT calculation may include smoothing the Kohn-Sham potential through a double filtering process inside the quantum nanostructure using a filter function, and defining the EMA envelope potential where atomic information reflects the potential using a function reflecting the Kohn-Sham potential profile itself on a quantum nanostructure surface/interface.

The creating of the EMA parameter through the DFT calculation may include smoothing a DFT dielectric function through a double filtering process inside the quantum nanostructure using a filter function, and defining an EMA envelop dielectric function where atomic information reflects the potential using a function reflecting a DFT dielectric function profile itself on a quantum nanostructure surface/interface.

The performing of the EMA calculation may include (1) calculating each electron and hole based on the extracted EMA parameter, (2) calculating a Coulomb potential and an exchange potential hidden for each of the calculated electron and hole, (3) re-defining an EMA potential in consideration of an external electric field together with the calculated hidden Coulomb potential and exchange potential, (4) re-calculating each electron and hole based on the re-defined EMA potential, (5) re-defining the Coulomb potential and the exchange potential for each electron and hole when a difference in a shape of calculated wave functions of each electron and hole is greater than a predetermined criterion, and (6) obtaining final electron and hole wave functions when the difference in the shape of the calculated wave functions of each electron and hole is less than the criterion.

The acquiring of the optical property may include acquiring photoluminescence intensity characteristics using an envelope function of the quantum nanostructure obtained through the first principle-derived effective mass approximation simulation calculation.

According to an exemplary embodiment, a first principle-derived effective mass approximation simulation system for accurate and efficient computational simulation of an optical property of a quantum nanostructure includes a creation device for creating an effective mass approximation (EMA) parameter through first principle density functional theory (DFT) calculation for a model nanostructure corresponding to a simulation target quantum nanostructure, a performance device for performing EMA calculation using the EMA parameter created through the DFT calculation, and an acquisition device for acquiring the optical property of the quantum nanostructure based on an electronic structure generated through the EMA calculation.

The quantum nanostructure may include a zero-dimensional quantum dot, a one-dimensional nanorod, and a two-dimensional nanoplatelet.

The EMA parameter may include effective electron and hole masses, a dielectric constant or a position-dependent dielectric function, a smoothed EMA envelope potential.

The creation device may perform first principle DFT calculation of the model nanostructure corresponding to the quantum nanostructure to extract a dielectric constant or a position-dependent dielectric function, electron and hole masses, and an EMA envelope potential obtained by smoothing a DFT-Kohn-Sham potential of the quantum nanostructure.

In the model nanostructure corresponding to the quantum nanostructure, an effective mass and the dielectric constant/function may be extracted from a nanoplate and a nanorod, and from a two-dimensional nanosheet with the most corresponding size and composition in a case of a quantum dot, and the EMA envelope potential may be extracted from a nanosheet infinitely extending in a two-dimension in the case of the nanoplate, a nanowire infinitely extending in a one-dimension in the case of the nanorod, and a zero-dimensional quantum dot in the case of the quantum dot.

The creation device may smooth the Kohn-Sham potential through a double filtering process inside the quantum nanostructure using a filter function, and define the EMA envelope potential where atomic information reflects the potential using a function reflecting the Kohn-Sham potential profile itself on a quantum nanostructure surface/interface.

The creation device may smooth a DFT dielectric function through a double filtering process inside the quantum nanostructure using a filter function, and define an EMA envelop dielectric function where atomic information reflects the potential using a function reflecting a DFT dielectric function profile itself on a quantum nanostructure surface/interface.

The performance device may perform the EMA calculation through (1) calculating each electron and hole based on the extracted EMA parameter, (2) calculating a Coulomb potential and an exchange potential hidden for each of the calculated electron and hole, (3) re-defining an EMA potential in consideration of an external electric field together with the calculated hidden Coulomb potential and exchange potential, (4) re-calculating each electron and hole based on the re-defined EMA potential, (5) re-defining the Coulomb potential and the exchange potential for each electron and hole when a difference in a shape of calculated wave functions of each electron and hole is greater than a predetermined criterion, and (6) obtaining final electron and hole wave functions when the difference in the shape of the calculated wave functions of each electron and hole is less than the criterion.

The acquisition device may acquire photoluminescence intensity characteristics using an envelope function of the quantum nanostructure obtained through the first principle-derived effective mass approximation simulation calculation.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
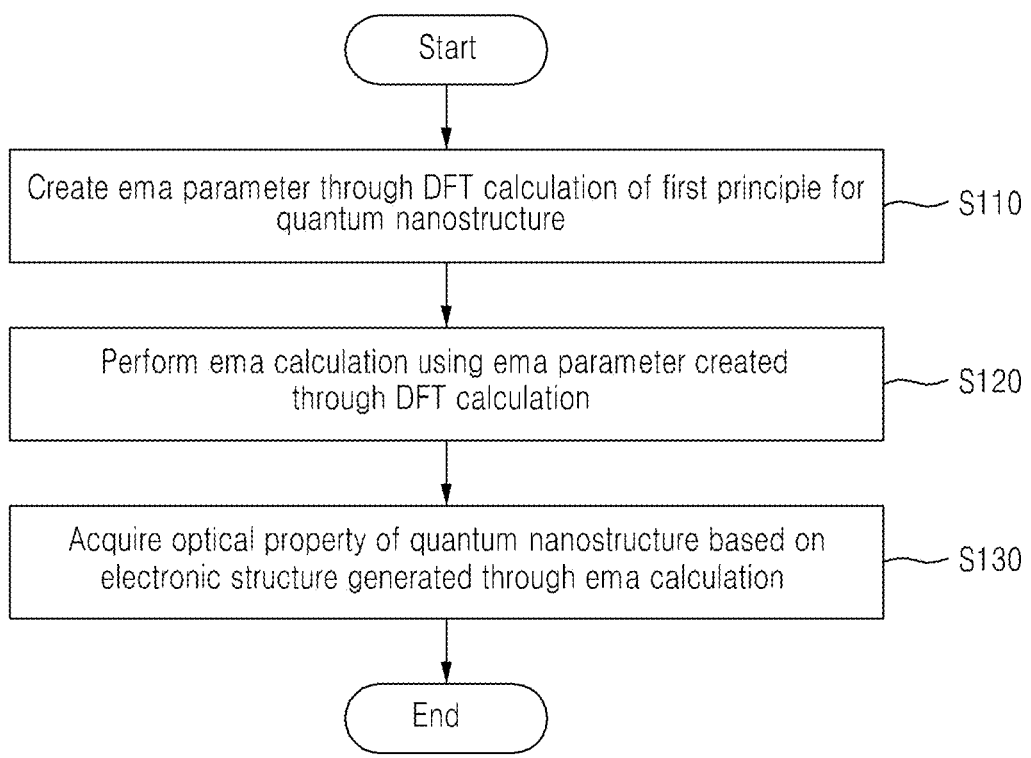
FIG. 1 shows an operational flowchart of a first principle-derived effective mass approximation simulation method according to an embodiment of the inventive concept.

Advantages and features of the inventive concept, and a method of achieving them will become apparent with reference to embodiments described below in detail together with the accompanying drawings. However, the inventive concept is not limited to the embodiments disclosed below, but may be implemented in various different forms. The present embodiments are provided to merely complete the disclosure of the inventive concept, and to merely fully inform those skilled in the art of the inventive concept of the scope of the inventive concept. The inventive concept is only defined by the scope of the claims.

The terminology used herein is for the purpose of describing the embodiments only and is not intended to limit the inventive concept. As used herein, the singular forms "a" and "an" are intended to include the plural forms as well, unless the context clearly indicates otherwise. The terms "comprises", "comprising", "includes", and "including" when used in this specification, specify the presence of the stated features, integers, operations, elements, and/or components, but do not preclude the presence or addition of one or greater other features, integers, operations, elements, components, and/or portions thereof.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, preferred embodiments of the inventive concept will be described in more detail with reference to the accompanying drawings. The same reference numerals are used for the same components in the drawings, and repeated descriptions of the same components are omitted.

Embodiments of the inventive concept are to extend an effective mass approximation (EMA) simulator based on a grid-based object-oriented real-space engine (OORE) for electronic structure calculation using an EMA parameter created from first principle calculation of a nanostructure.

Specifically, in reference density functional theory (DFT) calculation, the inventive concept extracts a nanoscopic dielectric constant, effective electron and hole masses, and additionally a Kohn-Sham (KS) potential. Then, an accurate and efficient EMA potential may be defined in an unambiguous manner through an envelope function of an atomistic KS potential. Although such approach should generally be applied to a finite sized-quantum nanostructure, including a zero-dimensional (0D) quantum dot, a one-dimensional (1D) quantum rod, and a two-dimensional (2D) nanoplatelet, the inventive concept focuses on optical properties of semiconductor nanorod and nanoplatelet, which have recently made significant experimental progress in synthesis. In particular, the inventive concept may identify that, for a 1D CdS/ZnS core/shell nanorod and a 2D CdSe nanoplatelet, a DFT-induced EMA approach of the inventive concept provides an optical gap in good agreement with experimentally measured data. For example, in the case of the CdS/ZnS nanorod, it may be seen that an optical gap of the nanorod is mainly determined by a nanorod diameter, and a photoluminescence (PL) intensity decreases as a nanorod length increases. In addition, the inventive concept may individually estimate effects of a bulk effective mass, a bulk dielectric constant, and an abrupt limit potential approximate value, and may identify that use of the abrupt limit potential has the most negative effect on a calculation accuracy.

Hereinafter, the inventive concept will be described in detail with reference to FIGS. 1 to 11.

FIG. 1 shows an operational flowchart of a first principle-derived effective mass approximation simulation method according to an embodiment of the inventive concept.

Figure 8:
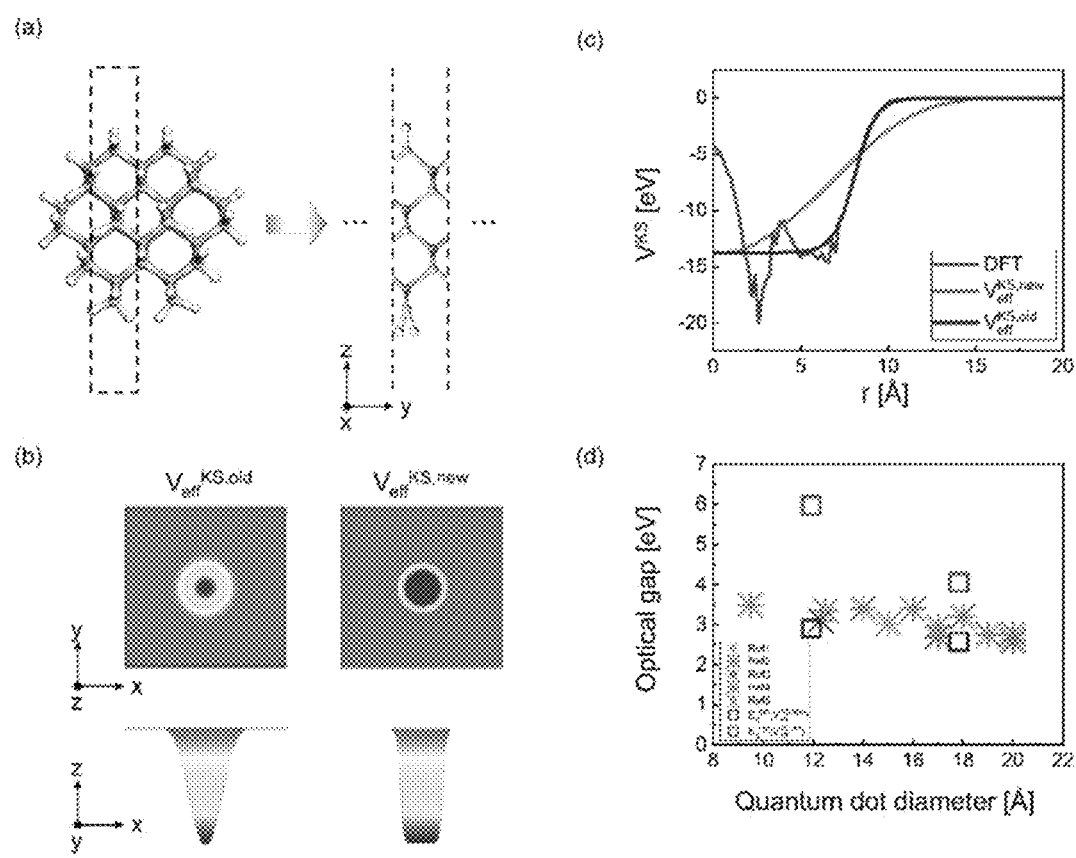
FIG. 8 shows experimental data regarding an example of application of a first principle-derived EMA quantum dot system according to an embodiment of the inventive concept.

The method of FIG. 1 is performed by a first principle-derived effective mass approximation simulation system according to an embodiment of the inventive concept shown in FIG. 8.

Referring to FIG. 1, in operation S110, the effective mass approximation (EMA) parameter is created through density functional theory (DFT) calculation of a first principle for a model nanostructure corresponding to a simulation target quantum nanostructure.

Operation S110 may extract the dielectric constant of the nanostructure, the effective electron and hole masses, and a smoothed Kohn-Sham potential by performing the first principle DFT calculation of the quantum nanostructure, and define the Kohn-Sham potential smoothed through a double filtering process of a Kohn-Sham potential using a filter function. In this connection, the quantum nanostructure may include a one-dimensional nanorod and a two-dimensional nanoplatelet.

In addition, operation S110 may use an object-oriented real-space engine (OORE) code to evaluate electronic structures and photoluminescence (PL) intensities of nanorods having different lengths and diameters when performing EMA calculation of the first principle of the quantum nanostructure.

Hereinafter, the DFT calculation and the EMA calculation will be described in detail.

First, when describing the DFT calculation, in a case of a one-dimensional (1D) CdS/ZnS core/shell nanowire and a two-dimensional (2D) CdSe nanosheet extending infinitely along a Z-axis or a slab extending infinitely along a X-Y-axis, operation S110 performs DFT calculation for a unit cell model within a local density approximation (LDA) exchange correlation function. The DFT calculation is performed with a VASP package. In this connection, a core electron is processed using a projector augmented wave scheme. In addition, a plane wave fundamental with a kinetic energy cutoff of 400 eV and a self-coherent cycle energy criterion of 10-4 eV is adopted. To avoid an artificial interaction with a surrounding image within a periodic boundary condition, a vacuum space of 20 Å or greater is inserted along a xy direction perpendicular to an axis of the 1D nanowire and a z direction perpendicular to a surface of the 2D slab. Furthermore, a Brillouin zone is sampled with a 1×1×10 Monkhorst-Pack grid for the CdS/ZnS nanowire and a 9×9×1 Monkhorst-Pack grid for the CdSe nanosheet. In the case of the nanowire, an edge state of a $(10\bar{1}0)$ surface is transferred by a pseudo-hydrogen atom. Specifically, a Cd or Zn dangling bond is transferred with a pseudo-bonding atom with a nuclear charge Z=1.5 electrons, and each S dangling bond is transferred by a pseudo-bonding atom with Z=0.5 electrons. In the case of the nanoplatelet, a (001) surface is coated with a protective film of acetate ligand, and the dielectric constant of the nanostructure is calculated using an optical dielectric function calculation module available within the VASP.

When describing the EMA calculation, operation S110 performs the EMA calculation using a grid-based object-oriented real-space engine (OORE) code to evaluate the electronic structures and the photoluminescence (PL) intensities of the nanorods having the different lengths and diameters. In this connection, operation S110 uses a higher order finite difference extension of a Laplacian operator as shown in [Equation 1] below.

$$\frac{d^2}{dx^2}f(x) = \sum_{j=-N}^{N} C_j f(x+jh) + O(h^{2N+2})$$ [Equation 1]

Here, "h" represents a grid gap, Cj represents a finite difference coefficient, and this is a multi-grid iteration minimization system for solutions of Schrödinger and Poisson equations.

An OORE framework may include a general tool for performing grid-based first principle DFT calculation, and may perform large-scale 3D EMA calculations (OOREQD) including an accurate and efficient exchange electron interaction simply by replacing a pseudo-potential with the EMA potential.

In operation S120, the EMA calculation is performed using the EMA parameter created through the DFT calculation. Thereafter, in operation S130, an optical property of the quantum nanostructure is acquired based on an electronic structure generated through the EMA calculation. Operation S130 may acquire photoluminescence intensity characteristics using an envelope function of the quantum nanostructure acquired through first principle-derived effective mass approximation simulation calculation.

In this connection, the EMA parameter may include the effective electron and hole masses, the dielectric constant, the smoothed Kohn-Sham potential, a length scaling factor, and an energy scaling factor.

Figure 2:
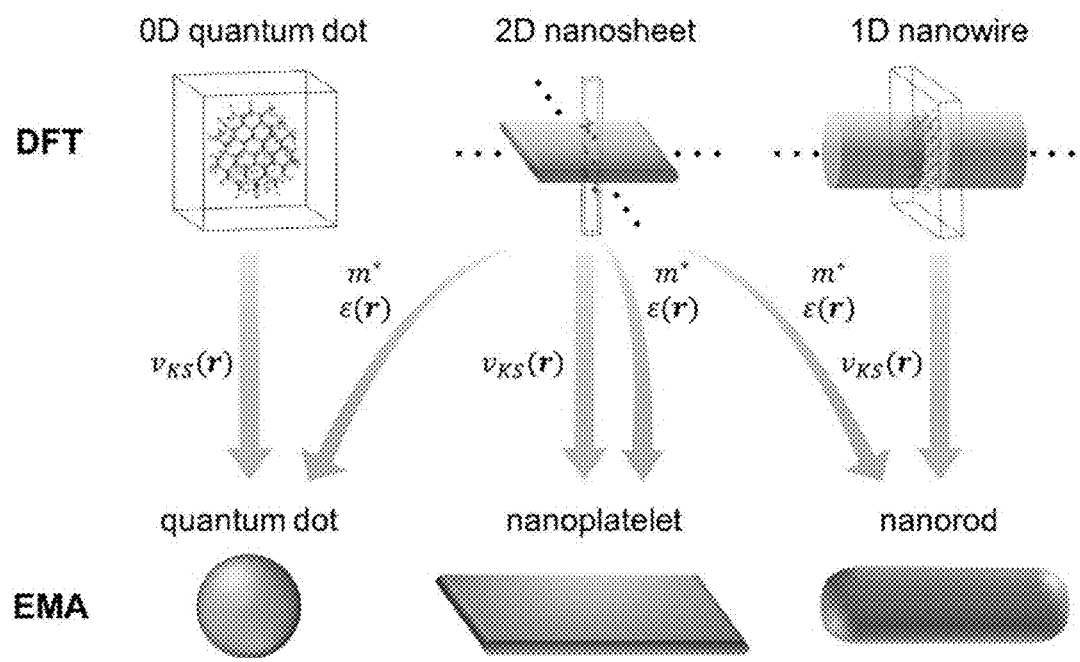
FIG. 2 shows a schematic diagram of a DFT-based EMA calculation strategy according to an embodiment of the inventive concept.

FIG. 2 shows a schematic diagram of a DFT-based EMA calculation strategy according to an embodiment of the inventive concept.

Referring to FIG. 2, envelope potentials are extracted from the zero-dimensional quantum dot, the one-dimensional nanowire, and the two-dimensional nanosheet and respectively reflected in a quantum dot, a nanorod, and a nanoplatelet. In the case of the quantum dot, the nanorod, and the nanoplatelet, the effective mass and the dielectric constant/function are extracted from the two-dimensional nanosheet that has the most corresponding size and composition.

Specifically, in a case of an 'ideal' low-dimensional nanostructure, first, the DFT calculation is performed, and then, an effective electron/hole mass $m_{e/h}^*$, a dielectric constant $\varepsilon$, and a KS potential $v^{KS}$ are calculated. For the effective mass and the dielectric constant, a length scale is set to $a_{e/h}^* = \varepsilon/m_{e/h}^*$ and an energy scale is set to $Ry_{e/h}^* = m_{e/h}^*/\varepsilon^2$. In this connection, the inventive concept defines an 'ideal' system as a nanostructure that extends infinitely along an unrestricted direction. For example, a finite quasi-1D nanorod and a quasi 2D nanoplatelet are considered as a 1D nanowire and a 2D nanosheet with a periodic boundary condition (PBC) along the z-direction and the xy-direction, respectively.

When describing an effective mass approximation formulation, the inventive concept performs a conduction band edge or (an electron) Schrödinger equation for an electromagnetic wave function $\psi_e$ and energy Ee within an isotropic EMA framework (a following [Equation 2]).

$$\left[-\frac{\hbar^2}{2m_e^*}\nabla^2 + v_{eff,e}^{KS}(r_e)\right]\psi_e(r_e) = E_e \psi_e(r_e)$$ [Equation 2]

In addition, as shown in [Equation 3] below, a valence band edge (a hole) Schrödinger for a hole waveform function and energy Eh is used separately.

$$\left[-\frac{\hbar^2}{2m_h^*}\nabla^2 + v_{eff,h}^{KS}(r_h)\right]\psi_h(r_h) = -E_h \psi_h(r_h)$$ [Equation 3]

Here, $\hbar$ represents a reduced Planck constant, $m_e^*$ represents an effective electron mass, and $m_h^*$ represents an effective hole mass.

It is emphasized that a core of the inventive concept is adoption of the EMA parameter derived from the first principle calculation performed on the representative model nanostructure. Importantly, in addition to the dielectric constant and the effective mass, the inventive concept introduces an effective potential $v_{eff,e}^{KS}/h$ in the reference DFT calculation. At a fundamental level, an 'exact' DFT KS equation for N electrons may be characterized as a Dyson equation for N−1 electrons, so that unoccupied orbitals obtained from KS calculation should physically account for number-conserving optical excitation of an N electron system. Accordingly, the inventive concept adopts $v_{eff,e}^{KS} = v_{eff,h}^{KS} = v_{eff}^{KS}$ in consideration of physical characteristics of the KS potential, and empirically determines an equation for a quasi-particle and an optical gap of the quantum nanostructure within the EMA by considering [Equation 2] and [Equation 3] as a quasi-particle equation [Equation 4] in consideration of a fact of starting with LDA DFT calculation contaminated with a self interaction error.

In this connection, once the hole and electron Schrödinger equations are solved, the inventive concept estimates an exciton transition energy or an optical gap $E_g^{opt}$.

$$E_g^{opt} = E_g^{qp} - E_X$$ [Equation 4]

Furthermore, the inventive concept calculates bandwidth edge transition energy or a quasi-particle $E_g^{qp}$ according to [Equation 5] below.

$$E_g^{qp} = E_{g,bulk}^{qp} + E_e - E_h$$ [Equation 5]

A CdS bulk quasiparticle gap $E_{g,bulk}^{qp}$ is obtained by adding an experimentally reported bulk optical band gap value $E_{g,bulk}^{opt}$ of 2.42 eV to calculated bulk exciton binding energy of 0.026 eV according to [Equation 6] below.

$$E_{X,bulk} = \frac{\mu e^4}{32\pi^2 \hbar^2 \varepsilon_r^2 \varepsilon_0^2}$$ [Equation 6]

Here $\varepsilon_r$ and $\varepsilon_0$ may represent a static bulk dielectric constant and a vacuum allowable amount, and μ may represent a reduced effective mass, and may be represented as in [Equation 7] below.

$$\frac{1}{\mu} = \frac{1}{m_e^*} + \frac{1}{m_h^*}$$ [Equation 7]

In the case of the nanorod, the inventive concept calculates exciton binding energy $E_X$ using [Equation 8].

$$E_X = \int\int \frac{|\psi_h(\vec{r}_h)|^2 |\psi_e(\vec{r}_e)|^2}{\varepsilon|\vec{r}_h - \vec{r}_e|} d\vec{r}_e d\vec{r}_h$$ [Equation 8]

Finally, an oscillator intensity for electron hole band edge exciton transition is calculated as [Equation 9].

$$O_{eh} = \frac{2m_e^*\omega}{\hbar}|\langle\psi_e|z|\psi_h\rangle|^2 \qquad \text{[Equation 9]}$$

Here, Oeh represents an oscillator intensity for electronic conversion from $\psi_e$ of Ee to $\psi_h$ of Eh.

Figure 3:
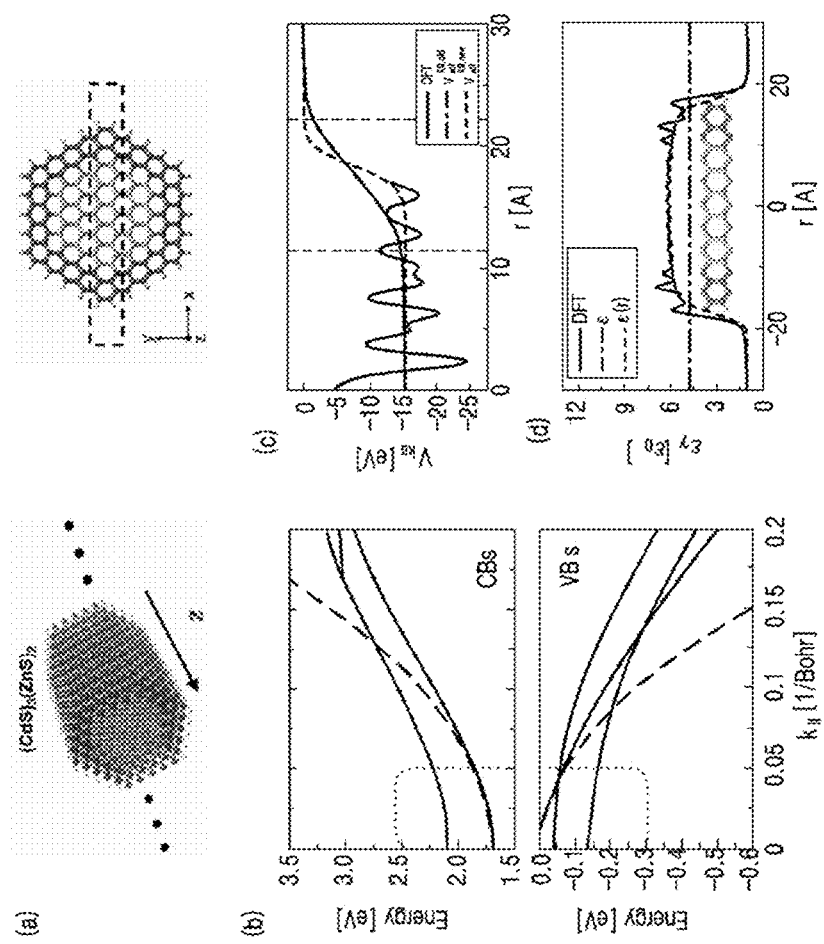
FIG. 3 shows experimental data on a method for extracting a parameter from DFT calculation according to an embodiment of the inventive concept.

FIG. 3 shows experimental data on a method for extracting a parameter from DFT calculation according to an embodiment of the inventive concept.

FIG. 3 is a method for performing first principle-derived EMA parameter extraction proposed in the inventive concept, and a one-dimensional nanorod structure with a core/shell structure of Cds/ZnS is calculated.

Referring to FIG. 3, in (a) in FIG. 3, a parameter may be extracted through periodic boundary condition DFT calculation for a nanowire structure infinite in the z direction for the nanorod structure. In (b) in FIG. 3, the effective mass may be calculated through parabolic approximation from valence band maximum (VBM) and conduction band minimum of an electronic band structure obtained as a result of the DFT calculation. In (c) in FIG. 3, vibrations at an atomic scale of the Kohn-Sham potential from a DFT structure are smoothed through post-processing. A smoothing method may include a double filtration method (a $2^{nd}$ avg. potential, a red line) and a surface/interface DFT potential fitting function (a new potential, a blue line) method. In (d) in FIG. 3, vibrations at an atomic scale of a position-dependent dielectric constant (DFT ε(r), a black line) from the DFT structure are smoothed through the post-processing. A smoothing method may include a double filtration method (ε(r), a green line).

When viewing papers that recently reported related experimental data, in the description of the Cds/ZnS core/shell nanorod, first, PBC DFT calculation is performed for the corresponding one-dimensional nanowire. This represents a nanowire model with mCdS and nZnS layers as (CdS)m(ZnS)n. As shown in (a) in FIG. 3, the inventive concept represents a $(CdS)_3(ZnS)_2$ core/shell nanowire with an optimized diameter of up to 3.5 nm in the DFT. In such a model, the inventive concept derives the effective electron (hole) mass $m_e^*(m_h^*)$ and the dielectric constant ε.

A DFT calculation dispersion of edges of conduction (a top panel) and valence (a bottom panel) bands of a $(CdS)_3(ZnS)_2$ nanowire is as shown in (b) in FIG. 3. However, it should be noted that a significant grid deformation effect has already been reflected in the band structure through DFT geometry optimization. A procedure for extracting the effective electron (hole) mass from a DFT-induced conduction (valence) band dispersion curve is also schematically described in (b) in FIG. 3. In this connection, a band dispersion region used for effective mass fitting is indicated by a shaded rectangle near a gamma (Γ)k point. To obtain the effective electron and hole masses, the inventive concept adopts a parabolic E-k dispersion relationship near Γ through [Equation 10] as follows.

$$E(k) = E_0 \pm \frac{\hbar^2 k^2}{2m_{e,h}^*} \qquad \text{[Equation 10]}$$

Here, $E_0$ represents an energy eigenvalue of the selected conduction band minimum (CBM) or valence band maximum (VBM) used for the effective mass fitting. The effective mass fitted for the CBM and the VBM of the $(CdS)_3(ZnS)_2$ nanowire is presented in [Table 1] below. A bulk CdS-induced electron mass and the effective hole mass are 0.2 $m_0$ and 0.7 $m_0$, respectively, but corresponding values induced from $(CdS)_3(ZnS)_2$ in a fitted equation ([Equation 11]) for a $(CdS)_3(ZnS)_2$ band edge represent 0.2 $m_0$ and 0.51 $m_0$, respectively. That is, the inventive concept determines that the bulk electron effective mass is converted into a nanowire electron effective mass $m_e^*$ but the effective hole mass $m_h^*$ is reduced by about 30% through the nanostructure.

It was identified that a dielectric constant of the CdS/ZnS nanowire summarized in [Table 1] is significantly reduced from 8.92, which is a bulk CdS dielectric constant value, by reduction of an electron blocking effect. Quantitatively, in the case of the $(CdS)_3(ZnS)_2$ core/shell nanowire, $\varepsilon_r^{zz}=2.3$ and $\varepsilon_r^{xx,yy}=2.2$ are represented along an axial direction and a radial direction, respectively. A small difference between the dielectric constants of the radial direction and the axial direction, which exhibits anisotropy negligible in a local dielectric blocking environment is noted. Therefore, the inventive concept adopts and uses an isotropic dielectric constant within the EMA calculation.

TABLE 1

| EMA parameters | Symbol (unit) | CdS bulk | $(CdS)_3(ZnS)_a$ nanowire |
|---|---|---|---|
| Effective electron mass | $m_e^*$ ($m_0$) | 0.20 | 0.20 |
| Effective hole mass | $m_h^*$ ($m_0$) | 0.70 | 0.51 |
| Dielectric constant | $\varepsilon_r$ | 8.92 | 2.30 |
| Length scaling factor: electron | $\alpha_e^*$ (Å) | 23.59 | 6.08 |
| Length scaling factor: hole | $\alpha_h^*$ (Å) | 6.74 | 2.39 |
| Energy scaling factor: electron | $R_e^*$ (eV) | 0.068 | 1.029 |
| Energy scaling factor: hole | $R_h^*$ (eV) | 0.239 | 2.623 |

Figure 4:
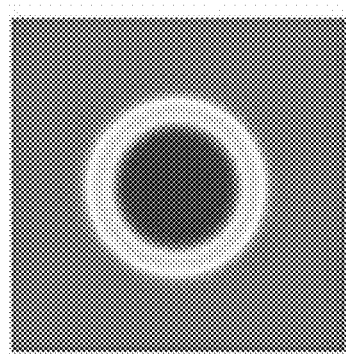
FIG. 4 shows a top view and a side view of an EMA effective potential according to an embodiment of the inventive concept.
Figure 4:
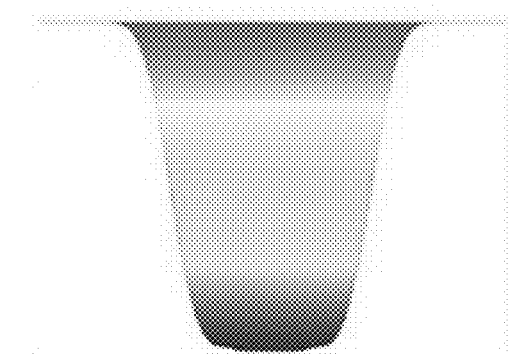
Figure 4:
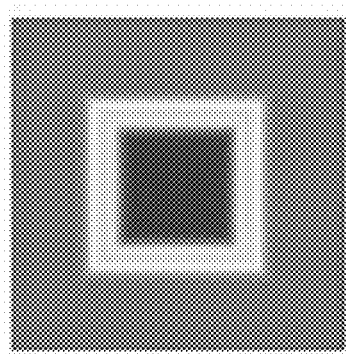
Figure 4:
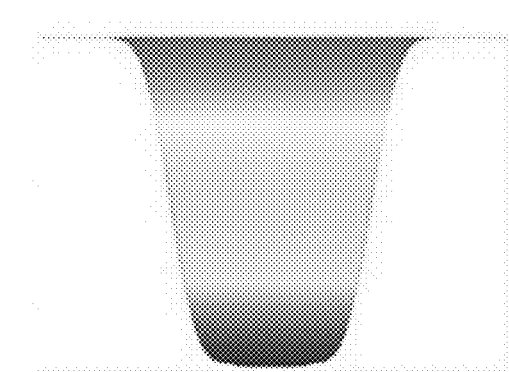
Figure 4:
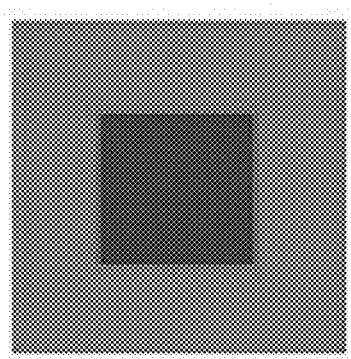
Figure 4:
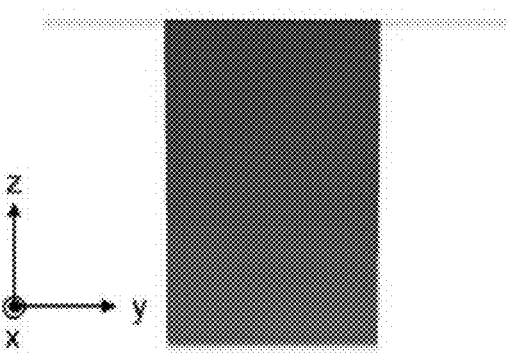
Figure 4:
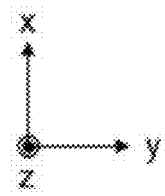
Figure 4:
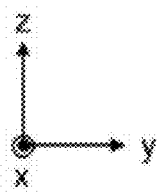

FIG. 4 shows a top view and a side view of an EMA effective potential according to an embodiment of the inventive concept.

A radial smoothed DFT KS potential shown in (c) in FIG. 3 is transformed into a cylindrical potential shape in (a) in FIG. 4 and a rectangular potential shape in (b) in FIG. 4.

As described above with reference to FIG. 3, in addition to the effective mass and the dielectric constant, utilization of KS potential $v_{KS}$ information for constructing an EMA effective potential $v_{eff}$ represents main characteristics of the approach of the inventive concept. Note that, in general, a limit potential shape is an important factor in determining electronic and optical properties of the quantum nanostructure. For example, it is possible to achieve suppression of an undesirable non-radioactive Auger process by theoretically relaxing the limit potential or by increasing a core volume. Therefore, many experimental efforts have recently been made to understand and optimize a material gradient at a core/shell interface.

In (c) and (d) in FIG. 3, the inventive concept presents a cylindrical average DFT KS potential and a corresponding EMA effective potential obtained for each of the $(CdS)_3(ZnS)_2$ nanowire case and a $(CdS)_3(ZnS)_1$ nanowire case. A smooth EMA potential is generated by obtaining an envelope function of the KS potential vibrating at the atomic scale using a double filtering process using a step function as the filter function.

$$w(r)=1/l\theta(l/2-|r|) \qquad \text{[Equation 11]}$$

In this connection, the inventive concept selects a smoothing parameter $l\approx7$ Å that is approximately a radial thickness of the two CdS (or ZnS) layers, and grid periodicity of a hexagonal nanowire grid geometry imposes a minimum $l\approx6.2$ Å by such selection. For example, changing a value of "l" to about ±1 Å changes a smoothed potential shape insignificantly, and a radially smooth 1D EMA potential profile is projected directly along a boundary of the quantum rod, so that the inventive concept adopts the rectangular shape and the cylindrical shape as shown in (a) and (b) in FIG. 4, respectively. As shown in (c) in FIG. 3, to identify importance of the DFT-based EMA effective potential, the inventive concept additionally adopts an abrupt potential together with a potential depth fixed to a DFT-induced EMA potential value. In this connection, based on the characteristics of the DFT KS equation mentioned above, the inventive concept uses the same EMA potential profile (with opposite signs) for the hole and electromagnetic wave functions.

Figure 5:
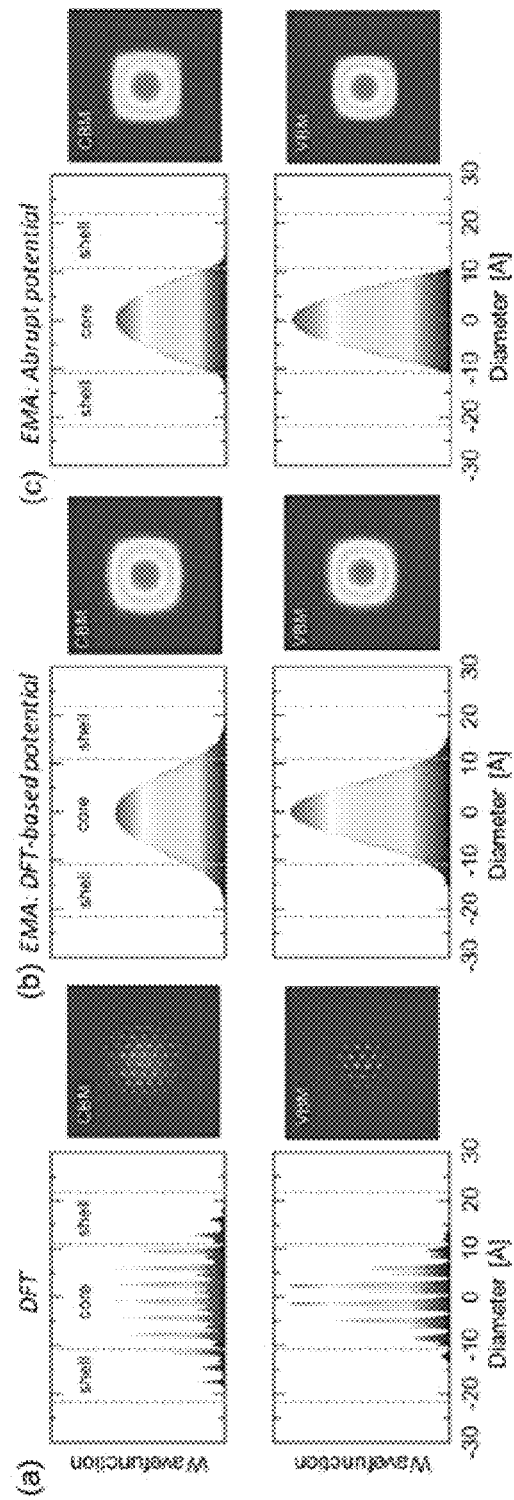
FIG. 5 shows experimental data for comparing waveform functions from DFT calculation and EMA calculation according to an embodiment of the inventive concept.

FIG. 5 shows experimental data for comparing waveform functions from DFT calculation and EMA calculation according to an embodiment of the inventive concept.

To identify a quality of the EMA potential used in the planning of the inventive concept, the inventive concept first analyzes radial EMA electron and hole waveform functions obtained by comparing [Equation 3] and [Equation 4] with the DFT counterpart. In (a) in FIG. 5, waveform functions of the CBM (top) and the VBM (bottom) obtained from the DFT calculation performed on the $(CdS)_3(ZnS)_2$ nanowire may be identified first. Next, in (b) in FIG. 5, corresponding waveform functions obtained from the DFT-based EMA calculation performed for a 12 nm long $(CdS)_3(ZnS)_2$ rectangular nanorod may be identified. In (c) in FIG. 5, corresponding waveform functions obtained by the abrupt EMA potential may be identified.

Overall, as may be expected from comparison between the DFT and the EMA potential, the inventive concept may identify that a vibration at the atomic scale of a DFT-induced wave function ((a) in FIG. 5) smoothly develops in EMA envelope waveform functions ((b) and (c) in FIG. 5). Next, when comparing EMA calculation based on the DFT-induced EMA potential and the abrupt EMA potential, it may be seen that the EMA system induced from the DFT of the inventive concept reproduces an envelope profile of a DFT waveform function much more closely. Both the electromagnetic wave and the hole wave functions penetrate into a shell region, and in particular, the electromagnetic wave function exhibits more delocalized characteristics. In one example, it may be concluded that the abrupt effective potential-based EMA method results in a waveform function that is too strongly confined within a core region ((c) in FIG. 5), and the DFT-based EMA approach of the inventive concept actually represents an improvement in describing the quantum nanostructure.

Figure 6A:
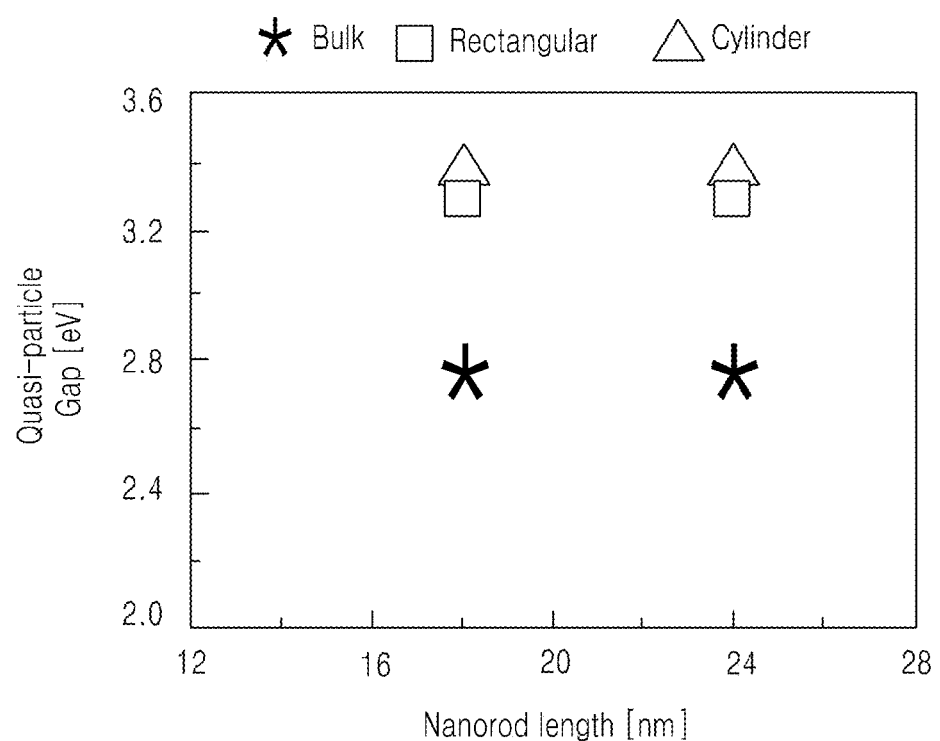
FIGS. 6A-C show experimental data for illustrating optical properties of CdS/ZnS nanorods by EMA calculation according to an embodiment of the inventive concept.
Figure 6B:
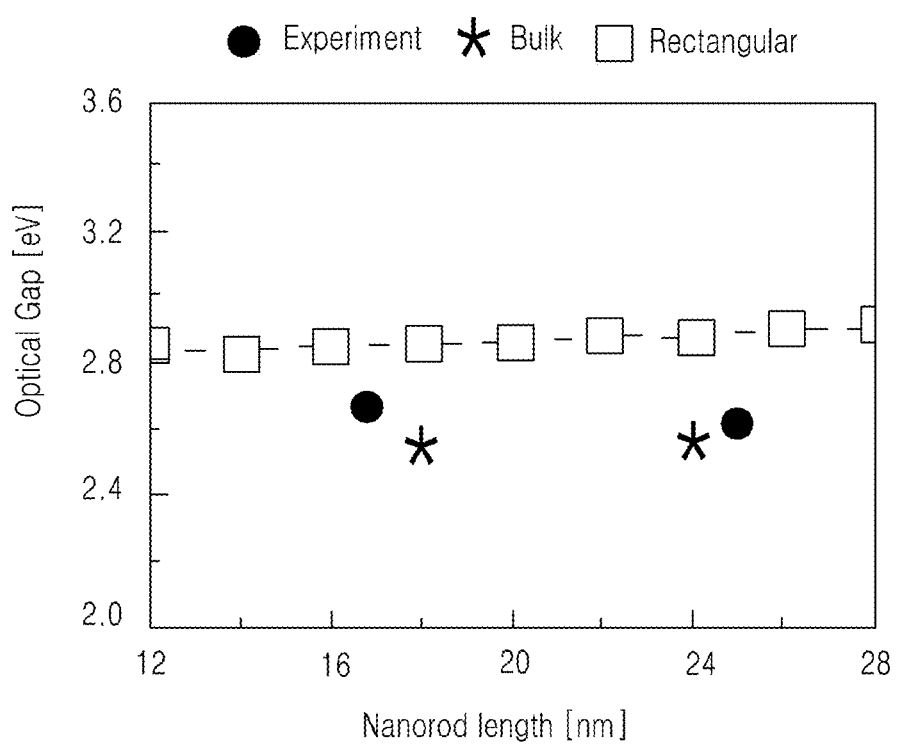
Figure 6C:
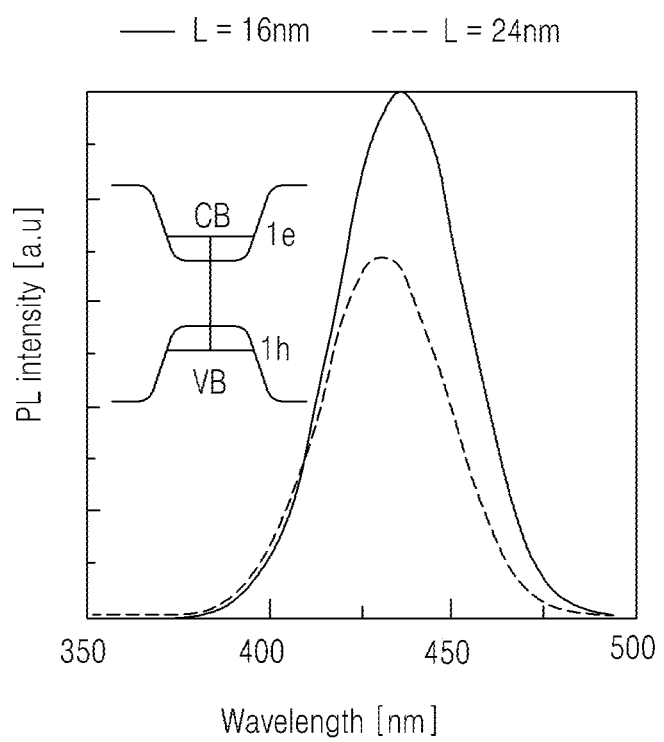

FIG. 6 shows experimental data for illustrating optical properties of CdS/ZnS nanorods by EMA calculation according to an embodiment of the inventive concept.

The inventive concept considers an energy difference of quantum rods calculated by the EMA approach.

In (a) in FIG. 6, the inventive concept presents quasiparticle gaps $E_g^{qp}$ of $(CdS)_3/(ZnS)_2$ nanorods of lengths of 18 nm and 24 nm in the cylindrical (a black triangle) and the rectangular (a blue square) limit potential shape respectively shown in (a) and (b) in FIG. 4. In both cases, $E_g^{qp}$ exhibits a minor change ($\lesssim 5$ meV) with respect to the nanorod length, indicating that $E_g^{qp}$ of the nanorod or an electron/hole eigenvalue Ee/–Eh is essentially determined by a smaller dimensional or radial quantum confinement. When comparing the $E_g^{qp}$ values obtained from the cylindrical EMA potential and the rectangular EMA potential, the inventive concept may identify that the former (the cylindrical EMA potential) is about 0.1 eV larger than the latter (the rectangular EMA potential) because of a slightly smaller cross-section in the cylindrical shape (in a case of a regular radius r, $\pi r^2$ not $4r^2$ in the rectangular rod shape). Consequently, because of close correspondence between the waveform function and the eigenvalue or the value in the cylindrical and rectangular shape limit potentials, only the rectangular EMA potential case is considered below.

For comparison, in (a) in FIG. 6, the inventive concept presents $E_g^{qp}$ values obtained from EMA calculation using the bulk effective mass and the dielectric constant together with an abrupt limit potential profile (a red star) shown in (c) in FIG. 4. This is smaller than that obtained from the DFT-based EMA calculation of about 0.6 eV (because of a potential floor area larger than that in the case of the DFT-induced potential), represents a weaker quantum limit, and provides an estimate of an error produced by an abrupt potential approximate value.

In (b) in FIG. 6, the inventive concept shows optical gap $E_g^{opt}$ values (circles filled in black) obtained by measuring $E_X$ in $E_g^{qp}$, and optical gap $E_g^{opt}$ values calculated by subtracting according to [Equation 4]. Within the nanostructure, quantum and dielectric confinement effects induce an enhanced electron-hole interaction, increasing the exciton binding energy $E_X$. Such characteristic of increasing $E_X$ at a nanoscale is resulted from a decrease in the dielectric constant or the electron blocking of the nanostructure compared to a bulk limit. For example, experimentally, it may be seen that the EX value of CdSe greatly increases from 15 meV of the bulk limit to about 240 meV in the nanorod and about 400 meV in the quantum dot. It is reported that an $E_X$ value of a CdS nanorod with a diameter in a range from 4 to 10 nm is in a range from 220 to 300 meV, which is greater than a bulk CdS EX value of 28 meV.

An $E_X$ value calculated in the DFT-based EMA calculation of $(CdS)_3(ZnS)_2$ according to [Equation 8] is in a range from 345 to 454 meV, which is applied with a trend of the reported $E_X$ value. Then, $E_g^{opt}$ apt values obtained from the DFT-based EMA approach (blue open squares) are in quantitative agreement with the experimental data. For reference, the inventive concept calculates an $E_X$ value using a following [Equation 12] for a spherical quantum dot with a radius R.

$$E_X = -\frac{1.786 e^2}{\varepsilon R} \quad \text{[Equation 12]}$$

In this connection, in a case of $(CdS)_3$ with a core diameter of about 2.3 nm, this leads to $E_X$=588 meV. This value, which is greater than the nanorod $E_X$ value (from 345 to 454 meV), makes sense in that the quantum limit should increase further as a nanorod geometry is switched to a quantum dot limit.

In one example, using the abrupt limit potential, the bulk effective mass, and the dielectric constant, an $E_X$ value in a range from 51 to 77 meV, which is smaller than the experimental value, and an $E_g^{opt}$ value of up to 200 meV (the red star) are obtained. Such $E_X$ value is a significant underestimation of the experimental value, represents shortcomings of the existing EMA approach, and quantifies an improvement achievable in the EMA system.

Using the numbers of electron and hole waveforms obtained from the DFT-based EMA calculation, oscillator intensity evaluation according to [Equation 9] and PL intensity estimation for CBM-to-VBM conversion are also performed. Accordingly, the inventive concept shows a PL intensity of the $(CdS)_3(ZnS)_2$ nanorod in a case of nanorod lengths of 16 nm and 24 nm in (c) in FIG. 6. In the case of the 24 nm nanorod, a PL peak position of 431 nm was obtained, and the PL peak position is very consistent with an experimental value. Accordingly, in the case of 16 nm nanorod, it may be seen that the PL intensity increases by about 30% as an axial quantum limit increases. In addition, it may be seen that a trend of the improved PL or a higher electron-hole recombination probability in a shorter nanorod is again in good agreement with the experimental data.

Figure 7:
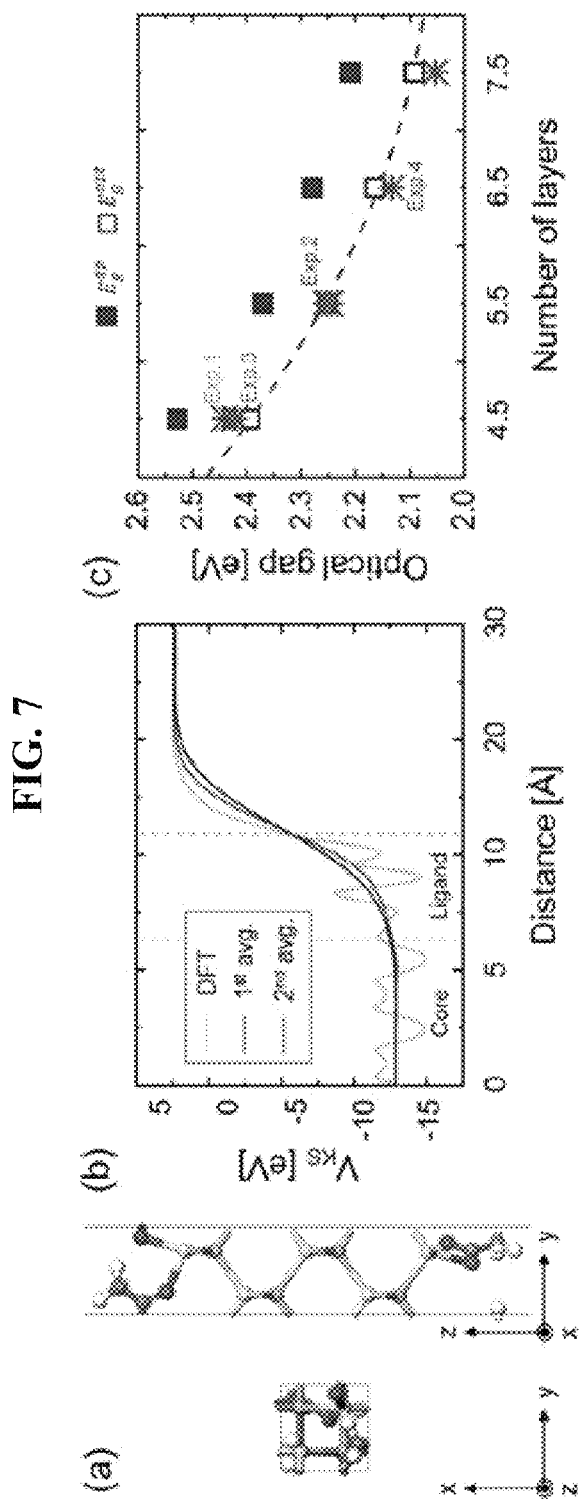
FIG. 7 shows EMA calculation results for an optical gap of a CdSe nanoplatelet according to an embodiment of the inventive concept.

FIG. 7 shows EMA calculation results for an optical gap of a CdSe nanoplatelet according to an embodiment of the inventive concept.

In the case of the CdS/ZnS nanorod case, despite a high degree of agreement between theory and experiment, the two $E_g^{qp}$ experimental data points are clearly very limited. To further identify generality and accuracy of developed formalism, the inventive concept next considers a CdSe nanoplatelet case in which accurate and efficient $E_X$ and $E_g^{opt}$ experimental data have been reported in recent years.

In (a) in FIG. 7, the inventive concept shows a unit cell of a reference 2D CdS nanosheet of 4.5 monolayer thickness covered with a protective film of acetate ligand. In this connection, an ideal reference nanostructure that preserves infinite periodicity along a free direction was adopted for the DFT calculation. Therefore, for EMA simulation of the CdSe nanoplatelet, a corresponding 2D CdSe slab was adopted and the DFT calculation was performed within the PBC along the xy direction. Then, the nanoscopic electron/hole effective mass $m_{e/h}^*$ and the dielectric constant $\varepsilon$ are extracted in the same manner as in the CdS/ZnS nanorod case, and the EMA parameter is summarized and presented in [Table 2] below. Another important element of the DFT-induced EMA system is extraction of an EMA limit potential from the reference DFT potential $v^{KS}$. The inventive concept shows a macroscopically smoothed EMA effective potential together with the KS potential in (b) in FIG. 7. By considering the periodicity of the grid along the z-direction when performing the double filtering procedure, the inventive concept adopts the smoothing parameter $l \approx 3$ Å (see [Equation 11]).

Using the EMA parameter induced from the DFT, the inventive concept then performed the EMA calculation for the CdSe nanoplatelet by changing the monolayer (ML) thickness from 4.5 ML (11.9 Å thickness, excluding the ligand) to 5.5 ML (14.9 Å) or 6.5 ML (18.0 Å). In this connection, the inventive concept modifies a backward dimension to 20 nm×20 nm such that a backward quantum confinement effect is negligible. In (c) in FIG. 7, calculated quasi-particle gap $E_g^{qp}$ (blue squares) and optical gaps $E_g^{opt}$ (blue empty square) values are presented. When compared with the experimental $E_g^{opt}$ data, the inventive concept finds superior agreement while reidentifying reliability and generality of a multi-scale approach.

TABLE 2

| Parameter | Symbol (unit) | CdSe bulk | CdSe nanosheet (4.5 ML) | CdSe nanosheet (6.5 ML) |
|---|---|---|---|---|
| Effective electron mass | $m_e^*$ ($m_0$) | 0.06 | 0.23 | 0.14 |
| Effective hole mass | $m_h^*$ ($m_0$) | 0.64 | 4.73 | 3.91 |
| Dielectric constant | $\varepsilon_r$ | 6.20 | 3.10 | 3.54 |
| Length scaling factor: electron | $\alpha_e^*$ (Å) | 10.67 | 20.57 | 13.38 |
| Length scaling factor: hole | $\alpha_h^*$ (Å) | 103.33 | 13.48 | 0.48 |
| Energy scaling factor: electron | $R_e^*$ (eV) | 0.002 | 0.02 | 0.304 |
| Energy scaling factor: hole | $R_h^*$ (eV) | 0.02 | 0.49 | 8.490 |

In addition, the inventive concept may systematically evaluate influence of individual factors in the bulk $m_e^*/m_h^*$, the bulk $\varepsilon$, and the abrupt limit potential approximate value when the EMA parameter and the limit potential shape are accurate and efficient.

[Table 3] shows the 4.5 ML CdSe nanoplatelet case. From [Table 3], it may be seen that $E_g^{qp}$ is most affected by the potential shape, whereas $E_X$ is more strongly influenced by the effective mass and the dielectric constant. In view of a coupled effect on $E_g^{opt}$ and [Equation 4], it may be identified that the abrupt potential shape is the most important error source. This will be a useful guideline for future calculation studies of the quantum nanostructure.

TABLE 3

| Value | Symbol (unit) | DFT derived | Bulk $m_{e/h}^*$ ($m_0$) | Bulk $\varepsilon_r$ | Abrupt potential |
|---|---|---|---|---|---|
| Quasi particle gap | $E_g^{qp}$ (eV) | 2.528 | 2.811 | 2.528 | 2.099 |
| Exciton binding energy | $E_X$ (eV) | 0.134 | 0.067 | 0.068 | 0.116 |
| Optical gap | $E_g^{opt}$ (eV) | 2.395 | 2.744 | 2.460 | 1.983 |

FIG. 8 shows experimental data regarding an example of application of a first principle-derived EMA quantum dot system according to an embodiment of the inventive concept.

Referring to FIG. 8, a process and a result of calculating an optical gap based on a thickness of a zero-dimensional CdSe structure using a first principle-derived EMA in the inventive concept are shown.

(a) in FIG. 8 shows the zero-dimensional CdSe structure (left) used for the potential extraction, and a two-dimensional structure of CdSe (right) for the effective mass and the position-dependent dielectric function extraction. (b) in FIG. 8, which shows two-dimensional profiles of the potentials extracted from the zero-dimensional CdSe structure, shows a $2^{nd}$ avg. potential (left) and new potential (right). (c) in FIG. 8, which shows one-dimensional profiles of the potentials extracted from the zero-dimensional CdSe structure, shows the $2^{nd}$ avg. potential (red) and the new potential (blue). In addition, (d) in FIG. 8 shows a result of comparing optical gaps using the $2^{nd}$ avg. potential (a red square) and the new potential (a blue square).

Figure 9:
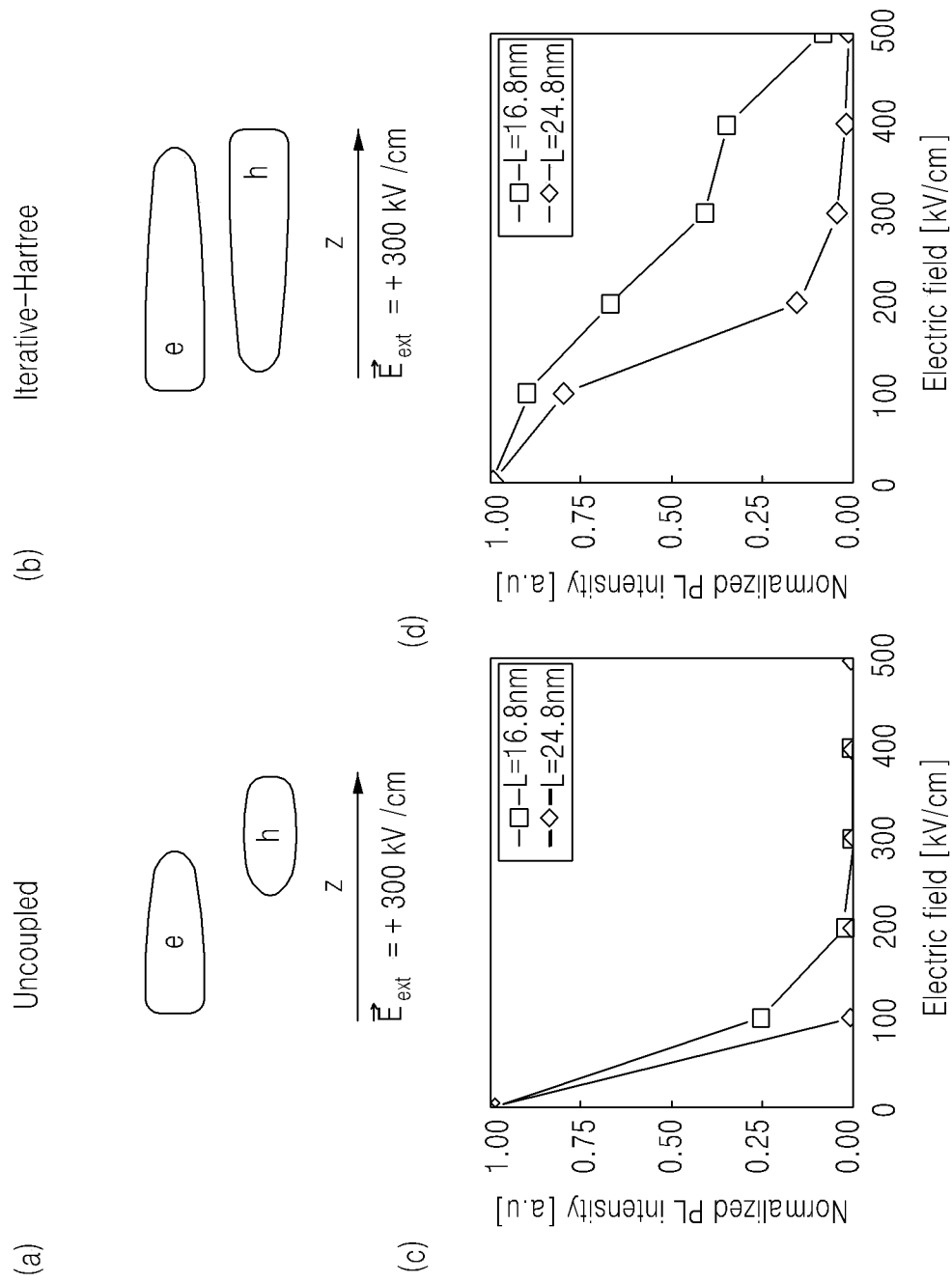
FIG. 9 shows experimental data comparing photoluminescence switching based on an electric field through first principle-derived iterative-Hartree EMA calculation according to an embodiment of the inventive concept.

FIG. 9 shows experimental data comparing photoluminescence switching based on an electric field through first principle-derived iterative-Hartree EMA calculation according to an embodiment of the inventive concept.

(a) in FIG. 9 shows movements of electrons and holes when receiving a 300 kV/cm electric field in the z-direction in a state in which the electrons and the holes do not have a correlation. (b) in FIG. 9 shows movements of the electrons and the holes when receiving the 300 kV/cm electric field in the z-direction in an iterative-Hartree EMA method. In addition, (c) in FIG. 9 shows a result of normalized photoluminescence switching based on the electric field in the state in which the electrons and the holes do not have the correlation, and (d) in FIG. 9 shows a result of normalized photoluminescence switching based on the electric field using the iterative-Hartree EMA method.

Figure 10:
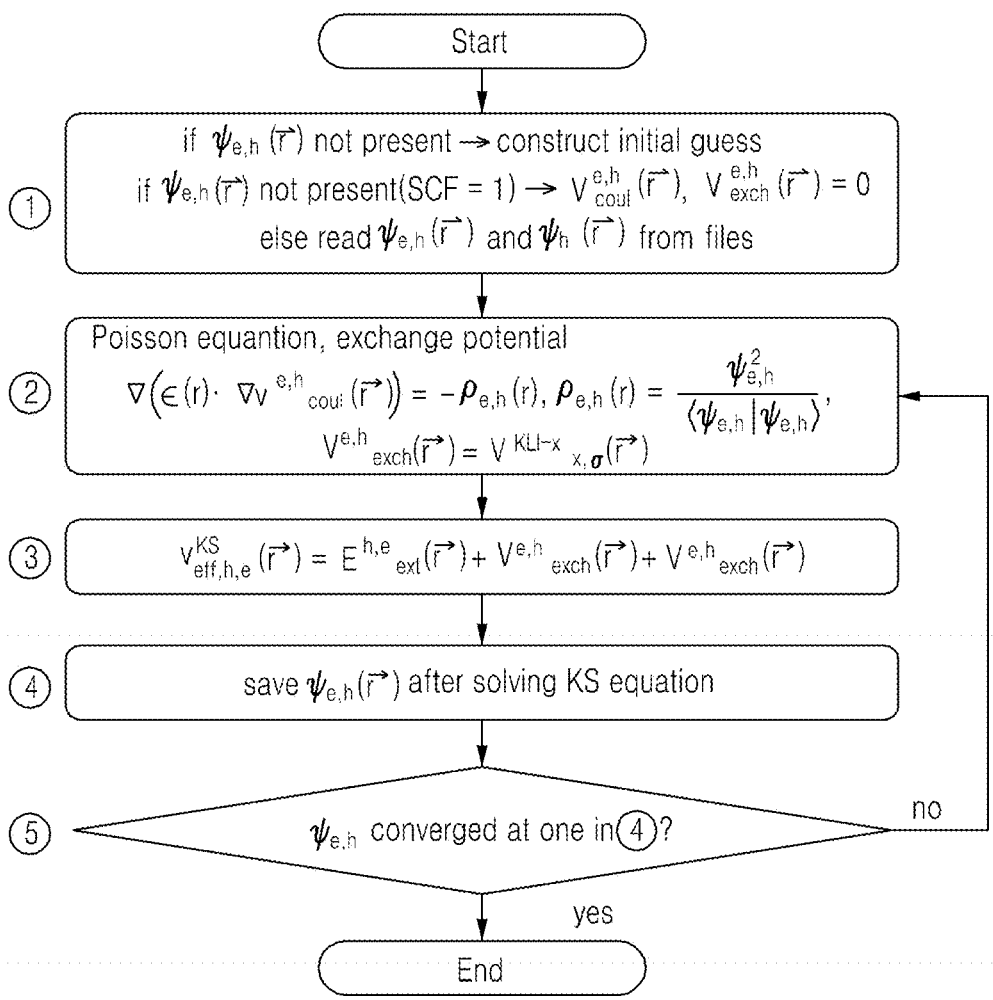
FIG. 10 is a flowchart showing an algorithm of first principle-derived iterative-Hartree EMA calculation according to an embodiment of the inventive concept.

FIG. 10 is a flowchart showing an algorithm of first principle-derived iterative-Hartree EMA calculation according to an embodiment of the inventive concept.

The inventive concept extracts an initial wave function for the iterative-Hartree EMA calculation in operation (1), and extracts a Coulomb potential and an exact-exchange potential for each of the corresponding electron and hole in operation (2). Thereafter, the inventive concept derives a final external potential by adding the potentials extracted in operation (2) to an external potential in operation (3), and extracts a wave function from the corresponding final external potential through the Schrödinger equation of the electron and the hole in operation (4). Accordingly, in operation (5), the inventive concept terminates the iterative-Hartree EMA calculation when the electron and the hole converge or moves to the process of operation (2) when the electron and the hole do not converge after the calculation is terminated.

Figure 11:
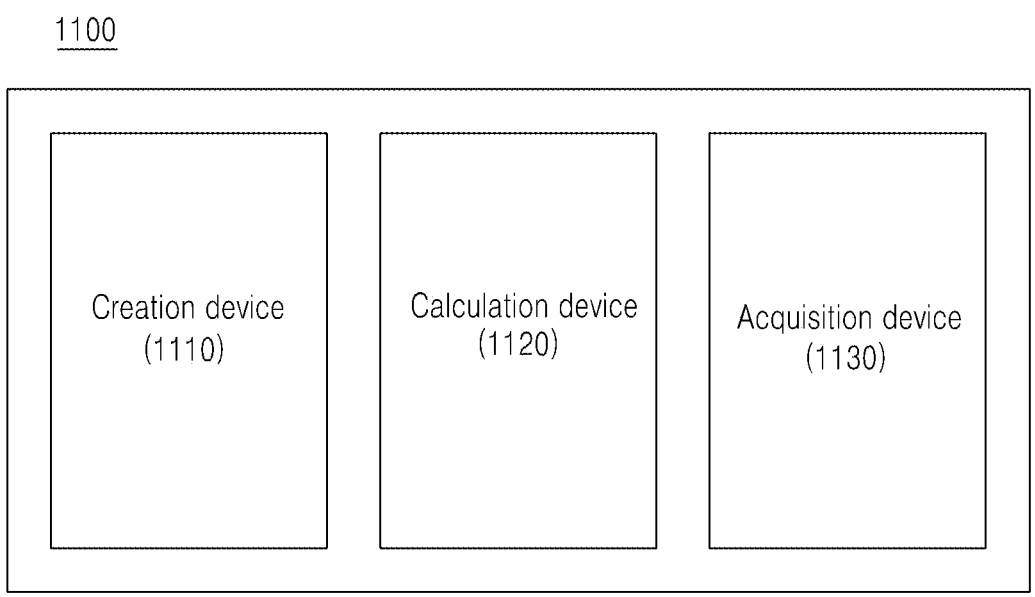
FIG. 11 is a block diagram illustrating a detailed configuration of a first principle-derived effective mass approximation simulation system according to an embodiment of the inventive concept.

FIG. 11 is a block diagram illustrating a detailed configuration of a first principle-derived effective mass approximation simulation system according to an embodiment of the inventive concept. FIG. 11 shows a conceptual configuration of a server or system that performs the first principle-derived effective mass approximation simulation method.

Referring to FIG. 11, a first principle-derived effective mass approximation simulation system 1100 according to an embodiment of the inventive concept includes a creation device 1110, a calculation device 1120, and an acquisition device 1130.

The creation device 1110 creates the effective mass approximation (EMA) parameter through the density functional theory (DFT) calculation of the first principle for the model nanostructure corresponding to the simulation target quantum nanostructure.

The creation device 1110 may extract the dielectric constant of the nanostructure, the effective electron and hole masses, and the smoothed Kohn-Sham potential by performing the first principle DFT calculation of the quantum nanostructure, and define the Kohn-Sham potential smoothed through the double filtering process of the Kohn-Sham potential using the filter function. In this connection, the quantum nanostructure may include the one-dimensional nanorod and the two-dimensional nanoplatelet.

In addition, the creation device 1110 may use the object-oriented real-space engine (OORE) code to evaluate the electronic structures and the photoluminescence (PL) intensities of the nanorods having the different lengths and diameters when performing the EMA calculation of the first principle of the quantum nanostructure.

The calculation device 1120 performs the EMA calculation using the EMA parameter created through the DFT calculation. Thereafter, the acquisition device 1130 acquires the optical property of the quantum nanostructure based on the electronic structure generated through the EMA calculation. The acquisition device 1130 may acquire the photoluminescence intensity characteristics using the envelope function of the quantum nanostructure acquired through the first principle-derived effective mass approximation simulation calculation.

In this connection, the EMA parameters may include the effective electron and hole masses, the dielectric constant, the smoothed Kohn-Sham potential, the length scaling factor, and the energy scaling factor.

Although, being omitted in the system of FIG. 11, a description of each component constituting FIG. 11 may include all the contents described with reference to FIGS. 1 to 10, which will be apparent to those skilled in the art.

The system or the device described above may be implemented with a hardware component, a software component, and/or a combination of the hardware component and the software component. For example, the device and the component described in the embodiments may be implemented using at least one general purpose computer or a special purpose computer, such as, for example, a processor, a controller, an arithmetic logic unit (ALU), a digital signal processor, a microcomputer, a field programmable gate array (FPGA), a programmable logic unit (PLU), a microprocessor, or any other device capable of executing and responding to instructions. The processing device may execute an operating system (OS) and at least one software application running on the operating system. The processing device may also access, store, manipulate, process, and generate data in response to the execution of the software. For convenience of understanding, there is a case in which one processing device is described as being used, but a person of ordinary skill in the art will recognize that the processing device may include a plurality of processing elements and/or a plurality of types of processing elements. For example, the processing device may include a plurality of processors or one processor and one controller. Other processing configurations, such as parallel processors, are also possible.

The software may include a computer program, a code, an instruction, or a combination of one or more thereof, and may construct the processing device or independently or collectively instruct the processing device to operate as desired. The software and/or the data may be permanently or temporarily embodied in any type of machine, a component, a physical device, virtual equipment, a computer storage medium or device, or a transmitted signal wave to be interpreted by or to provide the instruction or the data to the processing device. The software may be distributed over a networked computer system, and stored or executed in a distributed manner. The software and the data may be stored in at least one computer-readable recording medium.

The methods according to the embodiments may be implemented in a form of program instructions that may be executed through various computer means, and recorded in computer-readable media. The computer-readable media may also include, alone or in combination with the program instructions, data files, data structures, and the like. The program instructions recorded on the medium may be specially designed and configured for the embodiments, or may be known and available to those skilled in the art of computer software. Examples of computer-readable recording media include magnetic media such as a hard disk, a floppy disk, and a magnetic tape, optical media such as a CD ROM disk and a DVD, magneto-optical media such as a floptical disk, and hardware devices that are specially configured to store and perform program instructions, such as a read-only memory (ROM), a random access memory (RAM), a flash memory, and the like. Examples of the program instructions include both a machine code, such as produced by a compiler, and a higher level code that may be executed by the computer using an interpreter and the like. The described hardware devices may be configured to act as one or more software modules to perform the operations of the embodiments, or vice versa.

As described above, although the embodiments have been described with the limited embodiments and drawings, various modifications and variations are possible from the above description by those skilled in the art. For example, suitable results may be achieved even when the described technologies are performed in an order different from that of the described method, and/or when components in a described system, an architecture, a device, or a circuit are coupled or combined in a manner different from that of the described method and/or replaced or supplemented by other components or equivalents thereof.

Therefore, other implementations, other embodiments, and equivalents to the claims also fall within the scope of the following claims.

According to an embodiment of the inventive concept, the EMA simulator may be provided based on the grid-based object-oriented real-space engine (OORE) for the electronic structure calculation using the EMA parameter created from the first principle calculation of the nanostructure.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A first principle-derived effective mass approximation simulation method for accurate and efficient computational simulation of an optical property of a quantum nanostructure, the method comprising:
    creating an effective mass approximation (EMA) parameter through first principle density functional theory (DFT) calculation for a model nanostructure corresponding to a simulation target quantum nanostructure, wherein the EMA parameter is created to extend an EMA simulator based on a grid-based object-oriented real-space engine (OORE);
    performing EMA calculation using the EMA parameter created through the DFT calculation; and
    acquiring the optical property of the quantum nanostructure based on an electronic structure generated through the EMA calculation.

2. The method of claim 1, wherein the quantum nanostructure includes a zero-dimensional quantum dot, a one-dimensional nanorod, and a two-dimensional nanoplatelet.

3. The method of claim 1, wherein the EMA parameter includes effective electron and hole masses, a dielectric constant or a position-dependent dielectric function, a smoothed EMA envelope potential.

4. The method of claim 1, wherein the creating of the EMA parameter through the DFT calculation includes:
    performing first principle DFT calculation of the model nanostructure corresponding to the quantum nanostructure to extract a dielectric constant or a position-dependent dielectric function, electron and hole masses, and an EMA envelope potential obtained by smoothing a DFT-Kohn-Sham potential of the quantum nanostructure.

5. The method of claim 4, wherein, in the model nanostructure corresponding to the quantum nanostructure, an effective mass and the dielectric constant/function are extracted from a nanoplate and a nanorod, and from a two-dimensional nanosheet with the most corresponding size and composition in a case of a quantum dot, and the EMA envelope potential is extracted from a nanosheet infinitely extending in a two-dimension in the case of the nanoplate, a nanowire infinitely extending in a one-dimension in the case of the nanorod, and a zero-dimensional quantum dot in the case of the quantum dot.

6. The method of claim 4, wherein the creating of the EMA parameter through the DFT calculation includes:
    smoothing the Kohn-Sham potential through a double filtering process inside the quantum nanostructure using a filter function; and
    defining the EMA envelope potential where atomic information reflects the potential using a function reflecting the Kohn-Sham potential profile itself on a quantum nanostructure surface/interface.

7. The method of claim 4, wherein the creating of the EMA parameter through the DFT calculation includes:
    smoothing a DFT dielectric function through a double filtering process inside the quantum nanostructure using a filter function; and
    defining an EMA envelop dielectric function where atomic information reflects the potential using a function reflecting a DFT dielectric function profile itself on a quantum nanostructure surface/interface.

8. The method of claim 1, wherein the performing of the EMA calculation includes:
    calculating each electron and hole based on the extracted EMA parameter;
    calculating a Coulomb potential and an exchange potential hidden for each of the calculated electron and hole;
    re-defining an EMA potential in consideration of an external electric field together with the calculated hidden Coulomb potential and exchange potential;
    re-calculating each electron and hole based on the re-defined EMA potential;
    re-defining the Coulomb potential and the exchange potential for each electron and hole when a difference in a shape of calculated wave functions of each electron and hole is greater than a predetermined criterion; and
    obtaining final electron and hole wave functions when the difference in the shape of the calculated wave functions of each electron and hole is less than the criterion.

9. The method of claim 1, wherein the acquiring of the optical property includes:
    acquiring photoluminescence intensity characteristics using an envelope function of the quantum nanostructure obtained through the first principle-derived effective mass approximation simulation calculation.

10. A first principle-derived effective mass approximation simulation system for accurate and efficient computational simulation of an optical property of a quantum nanostructure, the system comprising:
    a creation device for creating an effective mass approximation (EMA) parameter through first principle density functional theory (DFT) calculation for a model nanostructure corresponding to a simulation target quantum nanostructure, wherein the EMA parameter is created to extend an EMA simulator based on a grid-based object-oriented real-space engine (OORE);
    a performance device for performing EMA calculation using the EMA parameter created through the DFT calculation; and
    an acquisition device for acquiring the optical property of the quantum nanostructure based on an electronic structure generated through the EMA calculation.

11. The system of claim 10, wherein the quantum nanostructure includes a zero-dimensional quantum dot, a one-dimensional nanorod, and a two-dimensional nanoplatelet.

12. The system of claim 10, wherein the EMA parameter includes effective electron and hole masses, a dielectric constant or a position-dependent dielectric function, a smoothed EMA envelope potential.

13. The system of claim 10, wherein the creation device performs first principle DFT calculation of the model nanostructure corresponding to the quantum nanostructure to extract a dielectric constant or a position-dependent dielectric function, electron and hole masses, and an EMA envelope potential obtained by smoothing a DFT-Kohn-Sham potential of the quantum nanostructure.

14. The system of claim 13, wherein, in the model nanostructure corresponding to the quantum nanostructure, an effective mass and the dielectric constant/function are extracted from a nanoplate and a nanorod, and from a two-dimensional nanosheet with the most corresponding size and composition in a case of a quantum dot, and the EMA envelope potential is extracted from a nanosheet infinitely extending in a two-dimension in the case of the nanoplate, a nanowire infinitely extending in a one-dimension in the case of the nanorod, and a zero-dimensional quantum dot in the case of the quantum dot.

15. The system of claim 13, wherein the creation device smooths the Kohn-Sham potential through a double filtering process inside the quantum nanostructure using a filter function, and defines the EMA envelope potential where atomic information reflects the potential using a function reflecting the Kohn-Sham potential profile itself on a quantum nanostructure surface/interface.

16. The system of claim 13, wherein the creation device smooths a DFT dielectric function through a double filtering process inside the quantum nanostructure using a filter function, and defines an EMA envelop dielectric function where atomic information reflects the potential using a function reflecting a DFT dielectric function profile itself on a quantum nanostructure surface/interface.

17. The system of claim 10, wherein the performance device performs the EMA calculation through:

calculating each electron and hole based on the extracted EMA parameter;
calculating a Coulomb potential and an exchange potential hidden for each of the calculated electron and hole;
re-defining an EMA potential in consideration of an external electric field together with the calculated hidden Coulomb potential and exchange potential;
re-calculating each electron and hole based on the re-defined EMA potential;
re-defining the Coulomb potential and the exchange potential for each electron and hole when a difference in a shape of calculated wave functions of each electron and hole is greater than a predetermined criterion; and
obtaining final electron and hole wave functions when the difference in the shape of the calculated wave functions of each electron and hole is less than the criterion.

18. The system of claim 10, wherein the acquisition device acquires photoluminescence intensity characteristics using an envelope function of the quantum nanostructure obtained through the first principle-derived effective mass approximation simulation calculation.

\* \* \* \* \*